US005716919A

United States Patent [19]
Sano

[11] Patent Number: 5,716,919
[45] Date of Patent: Feb. 10, 1998

[54] MILD CLEANSING FORMULATION WITH A HYDROXY-CONTAINING COMPOUND, A NONIONIC SURFACTANT AND AN ANIONIC SURFACTANT

[75] Inventor: Tomohiko Sano, Cincinnati, Ohio

[73] Assignee: The Andrew Jergens Company, Cincinnati, Ohio

[21] Appl. No.: 437,805

[22] Filed: May 9, 1995

[51] Int. Cl.$^6$ .................. C11D 1/83; C11D 3/20; C11D 3/22; A61K 7/02
[52] U.S. Cl. ............. 510/159; 510/130; 510/136; 510/137; 510/424; 510/427; 510/437; 510/466; 510/475; 510/470; 510/491; 510/505; 510/506
[58] Field of Search ............ 252/174.17, 174.21, 252/DIG. 5, DIG. 13, DIG. 1, 170, 173, DIG. 14; 510/130, 137, 136, 138, 159, 421, 422, 424, 505, 437, 491, 427, 466, 475, 470, 506

[56] References Cited

U.S. PATENT DOCUMENTS

| | | | |
|---|---|---|---|
| 4,597,893 | 7/1986 | Byford et al. | 252/354 |
| 5,211,941 | 5/1993 | Komori et al. | 424/70.12 |
| 5,462,691 | 10/1995 | Shimada et al. | 510/158 |
| 5,474,776 | 12/1995 | Koyanagi et al. | 424/401 |

FOREIGN PATENT DOCUMENTS

| | | |
|---|---|---|
| 62-288697 | 12/1987 | Japan . |
| 4-1040 | 1/1992 | Japan . |
| 4-91018 | 3/1992 | Japan . |
| 5-208905 | 8/1993 | Japan . |
| 6-16253 | 1/1994 | Japan . |
| 6-16254 | 1/1994 | Japan . |

OTHER PUBLICATIONS

Derwent Abstracts, AN-90-196834/26, JP-2-129110, May 17, 1990.
Derwent Abstracts, AN-91-136882/19, JP-3-074313, Mar. 28, 1991.
Derwent Abstracts, AN-91-248682/34, JP-3-161428, Jul. 11, 1991.
Derwent Abstracts, AN-91-373540/51, JP-3-251516, Nov. 11, 1991.
Derwent Abstracts, AN-92-147947/18, JP-4-091018, Mar. 24, 1992.
Japan Abstracts, AN-92-001040, JP-4-1040, Jan. 6, 1992.
Derwent Abstracts, AN-92-180847/22, JP-4-120015, Apr. 21, 1992.
Derwent Abstracts, AN-92-361893/44, JP-4-264015, Sep. 18, 1992.
Derwent Abstracts, AN-92-361980/44, JP-4-264186, Sep. 18, 1992.
Derwent Abstracts, AN-92-384880/47, JP-4-282303, Oct. 7, 1992.
Derwent Abstracts, AN-74-55788V/31, JP-49-019046, Feb. 20, 1974.
Derwent Abstracts, AN-93-049798/06, JP-5-001299, Jan. 8, 1993.
Derwent Abstracts, AN-75-83905W/51, JP-50-077289, Jun. 24, 1975.
Derwent Abstracts, AN-93-191423/24, JP-5-117138, May 14, 1993.
Derwent Abstracts, AN-77-52919Y/30, JP-52-070035, Jun. 10, 1977.
Derwent Abstracts, AN-93-297778/38, JP-5-208905, Aug. 20, 1993.
Derwent Abstracts, AN-78-59815A/33, JP-53-080460, Jul. 15, 1978.
Derwent Abstracts, AN-80-28435C/16, JP-55-033447, Mar. 8, 1980.
Derwent Abstracts, AN-80-28436C/16, JP-55-033448, Mar. 8, 1980.
Derwent Abstracts, AN-81-55831D/31, JP-56-070098, Jun. 11, 1981.
Derwent Abstracts, AN-82-47087E/23, JP-57-070824, May 1, 1982.
Derwent Abstracts, AN-83-16323k/07, JP-58-003630, Jan. 10, 1983.
Derwent Abstracts, AN-83-835358/49, JP-58-183608, Oct. 26, 1983.
Derwent Abstracts, AN-84-065028/11, JP-59-020213, Feb. 1, 1984.
Derwent Abstracts, AN-84-253066/41, JP-59-152306, Aug. 31, 1984.
Derwent Abstracts, AN-85-052433/09, JP-60-008398, Jan. 17, 1985.
Derwent Abstracts, AN-94-061968/08, JP-6-016523, Jan. 25, 1994.
Derwent Abstracts, AN-94-061969/08, JP-6-016524, Jan. 25, 1994.
Derwent Abstracts, AN-86-059653/09, JP-61-012603, Jan. 21, 1986.
Derwent Abstracts, AN-86-091194/14, JP-61-037709, Feb. 22, 1986.
Derwent Abstracts, An-86-287482/44, JP-61-209035, Sep. 17, 1986.
Derwent Abstracts, AN-87-075511/11, JP-62-027500, Feb. 5, 1987.
Derwent Abstracts, AN-87-113259/16, JP-62-059698, Mar. 16, 1987.
Derwent Abstracts, AN-88-026392/04, JP-62-288673, Dec. 15, 1987.
Derwent Abstracts, AN-89-018044/03, JP-63-287718, Nov. 24, 1988.
Derwent Abstracts, AN-91-354375/49, CA-2038251, Sep. 15, 1991.

(List continued on next page.)

*Primary Examiner*—Ardith Hertzog
*Attorney, Agent, or Firm*—Oblon, Spivak, McClelland, Maier & Neustadt, P.C.

[57] ABSTRACT

The invention relates to a mild cleansing composition with good cleansability, good rinseability and a clean after feeling. The cleaning composition contains a compound bearing at least one hydroxy moiety, a hydrophilic nonionic surfactant, and no more than 55% water. This mild cleansing composition is useful for cleansing cosmetics, as well as a lubricant for the skin for massage.

35 Claims, No Drawings

OTHER PUBLICATIONS

Derwent Abstracts, AN-81-91208D/50, DD-150759, Sep. 16, 1981.
Derwent Abstracts, AN-87-349539/50, DE-3619358, Dec. 10, 1987.
Derwent Abstracts, AN-88-271727/39, DE-3707711, Sep. 22, 1988, (2 pages).
Derwent Abstracts, AN-94-043743/06, DE-4225136, Feb. 3, 1994.
Derwent Abstracts, AN-85-117849/20, EP-141732, May 15, 1985, (2 pages).
Derwent Abstracts, AN-86-170937/27, EP-186453, Jul. 2, 1986.
Derwent Abstracts, AN-86-340531/52, EP-206144, Dec. 30, 1986.
Derwent Abstracts, AN-87-095199/14, EP-217105, Apr. 8, 1987.
Derwent Abstracts, AN-87-179343/26, EP-227012, Jul. 1, 1987.
Derwent Abstracts, AN-91-111357/16, EP-422862, Apr. 17, 1991.
Derwent Abstracts, AN-91-247089/34, EP-442371, Aug. 21, 1991.
Derwent Abstracts, AN-92-017860/03, EP-466236, Jan. 15, 1992.
Derwent Abstracts, AN-93-086797/11, EP-531684, Mar. 17, 1993.
Derwent Abstracts, AN-84-233079/38, GB-2136445, Sep. 19, 1984.
Derwent Abstracts, AN-87-052125/08, GB-2179052, Feb. 25, 1987, (2 pages).
Derwent Abstracts, AN-85-110081/18, US-4511563, Apr. 16, 1985.
Derwent Abstracts, AN-91-237391/32, US-5034220, Jul. 23, 1991.
Derwent Abstracts, AN-84-184409/30, HUT-030706, Mar. 28, 1984.
Derwent Abstracts, AN-77-30482Y/17, SU-511083, Nov. 18, 1976.
Derwent Abstracts, AN-88-285397/40, WO-8806881, Sep. 22, 1988, (2 pages).
Derwent Abstracts, AN-92-131861/16, WO-9204882, Apr. 2, 1992.
Derwent Abstracts, AN-93-288395/36, WO-9317088, Sep. 2, 1993.
Derwent Abstracts, AN-94-357765/44, WO-9424863, Nov. 10, 1994.
Derwent Abstracts, AN-94-357863/44, WO-9425001, Nov. 10, 1994.

MILD CLEANSING FORMULATION WITH A HYDROXY-CONTAINING COMPOUND, A NONIONIC SURFACTANT AND AN ANIONIC SURFACTANT

BACKGROUND OF THE INVENTION

1. Field of the Invention

The invention relates to a mild cleansing composition with good cleansability, good rinseability and a clean after feeling. This mild cleansing composition is useful for cleansing cosmetics and as a lubricant for the skin for massage.

2. Discussion of the Background

Cleansing cosmetics are widely used to remove dirt or makeup from the skin. They are applied to the skin, left on for a period of time, and then removed.

Conventional commercially available compositions for the removal of dirt or makeup from skin contain an oleaginous liquid. These materials are oil based, water-in-oil emulsions.

Oil based compositions, as well as water-in-oil and oil-rich oil-in-water emulsions, often have good cleansing properties, but are not completely removed from the skin by rinsing, and leave the skin oily or greasy. Traditionally, the oil based or water-in-oil emulsions are wiped off with tissue paper, followed by a facial cleanser. However, removal with tissue paper also removes the horny cells of the skin, and the oil containing composition soaks through the tissue paper leaving the fingers greasy and sticky.

Water-rich emulsions, which contain less oil, do not need to be removed with tissue paper and leave the skin feeling fresh. However, water-rich emulsions are not effective cleansing agents.

SUMMARY OF THE INVENTION

Accordingly, one object of the present invention is to provide a novel cleansing composition which is mild, has good cleansing properties, and is easily rinsed off with water.

Another object of the present invention is to provide a cleansing composition which does not contain oil, and leaves the skin with a clean feeling after removal.

The present invention is a cleansing composition which contains:

(a) a compound bearing at least one hydroxy moiety, selected from the group consisting of a polyhydric alcohol, an aldohexose, an aldopentose and sucrose;

(b) a hydrophilic nonionic surfactant; and (c) no more than 55%, by weight, of water.

Cleansing compositions of the present invention are applied to the skin to remove dirt or makeup from the surface of the skin. After application, they can be rinsed off with water, without leaving an oil or greasy feeling residue on the skin. After rinsing, the skin feels clean and fresh.

Cleansing compositions of the invention are applied to the skin, spread evenly on the skin, and left for a period of time. Additional amounts may be added to the skin as needed. Finally, they can be rinsed away with water. After rinsing they leave the skin fresh and clean, having removed dirt, oil and make-up well, without a greasy or sticky feeling.

DESCRIPTION OF THE PREFERRED EMBODIMENTS

The invention polyhydric alcohols, aldohexoses and aldopentoses, as well as sucrose, are all commercially available, or can be made by methods well known to those of ordinary skill in the art. The hydrophilic nonionic surfactants are also commercially available, or can be made by methods well known to those of ordinary skill in the art.

All percentages herein are by weight, unless otherwise specified, based on the total weight of the composition. All molecular weights are weight average molecular weights, unless otherwise specified.

Water may be added to the invention cleansing compositions. No more than 55% water is normally used in the cleansing compositions. Preferably, 5–55% water is used, more preferably 10–45% water, but including all values and all ranges therebetween.

The compound bearing at least one hydroxy moiety used in the invention cleansing composition is a polyhydric alcohol, an aldohexose, an aldopentose, or sucrose. The compound bearing at least one hydroxy moiety is used in an amount of from 25–80%, by weight, preferably 35–75%, by weight, but including all values and all ranges therebetween. Also, two or more compounds bearing at least one hydroxy moiety can be used in the cleansing composition.

The polyhydric alcohols are not particularly restricted. Preferred polyhydric alcohols are sorbitol, polyethylene glycol with a weight average molecular weight of at least 1000, xylitol, maltitol, mannitol, glycerine, arabitol, erythritol, diglycerine, triglycerine, hexaglycerine, decaglycerine, polyoxyethylene methyl glucoside, 1,3-butylene glycol, hexylene glycol, dipropylene glycol, polyethylene methyl glucoside and polypropylene methyl glucoside.

The aldohexose used in the invention cleansing composition is not particularly restricted. Preferred aldohexoses are glucose, mannose, galactose and fructose.

The aldopentoses of the present invention are not particularly restricted. Preferred aldopentose are arabinose, xylose, ribose and lyxose.

Particularly preferred compounds bearing at least one hydroxy moiety lower the HLB (hydrophilic lipophilic balance) value of the nonionic surfactant, such as sorbitol, polyethylene glycol with a molecular weight of at least 1000, xylitol, erythritol and glycerine. These compounds also lower the cloud point of the nonionic surfactants.

The hydrophilic nonionic surfactant of the present invention is not particularly restricted. In the inventive cleansing compositions, they preferably have an HLB value of more than 10. Preferred hydrophilic nonionic surfactants are polyalkoxylated sorbitan esters, polyalkoxylated alcohols, polyalkoxylated triglycerides and dimethicone copolymers. The hydrophilic nonionic surfactant is typically used in 5–75%, by weight, preferably 5–55%, by weight, but including all ranges and values therebetween. It is also possible to use 25–55% of the hydrophilic nonionic surfactant. Preferred polyalkoxylated compounds are polyethoxylated, polypropoxylated, polybutoxylated, polypentoxylated and polyhexoxylated compounds, especially polyethoxylated compounds. Only one nonionic surfactant is necessary, but two or more may also be used. In addition other surfactants may be added to the cleansing composition, such as anionic surfactants, preferably up to 10%, more preferably 0.01–5%, even more perferably 0.1–2% by weight.

Preferred polyethoxylated sorbitan esters are fatty acid esters, especially those fatty acids which have a branched or straight chain alkyl group of 12–18 carbon atoms. Preferred polyethoxylated sorbitan esters have 15–80, more preferably 15–40, ethoxy moieties per molecule.

Preferred polyethoxylated alcohols have a branched or straight chain alkyl group of 12–22 carbon atoms. More preferably, they also have 20–30 ethoxy moieties per molecule.

Preferred polyethoxylated triglycerides are made from coconut oil, or hydrogenated castor oil. Preferably, the polyethoxylated triglycerides have 40–80 ethoxy moieties per molecule.

Dimethicone copolymers or copolyols are adducts of dimethylpolysiloxane and polyoxyethylene. Preferred dimethicone copolymers used in the cleansing compositions have the formula:

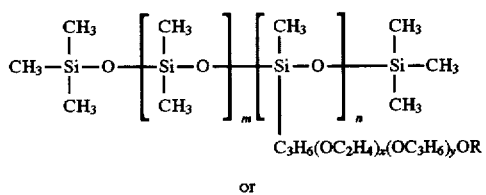

or

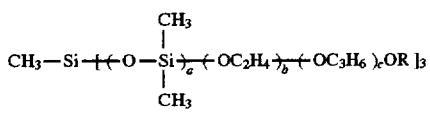

where

- R is a hydrogen atom, or an alkyl group with a strait or branched chain, having 1–30, preferably 6–24, more preferably 12–18, carbon atoms;
- m and n are integers, independently 1–80, preferably 5–60, more preferably 5–40;
- x and y are integers, independently 5–80, preferably 5–40;
- a is an integer, 1–80, preferably 5–60, more preferably 5–30; and
- b and c are integers, independently 5–80, preferably 5–40.

It is unnecessary to add an oil or oleaginous substance to the cleansing compositions, and preferably, the cleansing compositions do not contain an oleaginous liquid. Because the compositions do not contain oil, they will not be emulsions, but rather single phase liquids. To obtain stable formulations, a water insoluble nonionic surfactant, as well as sorbitan monostearate, a fatty alcohol or polyglycerin fatty acid ester monoglyceride, can be added, in an amount of no more than 5%, preferably 0.1–3%, by weight. Finally, cleansing compositions of the invention will wash off human skin with water alone, without leaving a greasy or oily residue.

The cleansing compositions of the invention can also be used as carriers for certain active agents, for example UV absorbers, perfumes, fragrances, dyes, pigments, antiseptics and/or insect repellents. Other additives may also be incorporated into the cleansing compositions, such as opacifiers, stabilizers, vitamins, proteins, salts, skin conditioners, preservatives and/or antioxidants.

Other features of the invention will become apparent in the course of the following descriptions of exemplary embodiments which are given for illustration of the invention and are not intending to be limiting thereof:

EXAMPLES

Tables 1–7 show a variety of compositions of the present invention (Examples) and Comparative samples. The amounts are all in parts by weight, except where noted. POE(20):sorbitan monostearate and monooleate are made by High Point Chemical (NC); POE(40) and POE(60) hydrogenated castor oil and, Na and Mg laureth sulfate, are made by Henkel Corporation (N.J.); POE(20) and POE(25) Octyldodecanol are made by Kao Corporation (JP); POE (20) Sorbitan monoisostearate is made by Nikko Chemical Corp. (Japan); dimethicone copolyol is made by Nihon Unikah (Japan); and Na Cocoyl methyl taurate is made by Finetex, Inc. (USA).

The compositions were evaluated for cleansing as follows:

Ordinary lipstick was applied to the forearm in the shape of a circle with about a 3 cm diameter. One milliliter of test sample was applied, about five minutes after the lipstick was applied, in the center of the circle and gently rubbed in a circular motion about 10 times. Next, the lipstick was rinsed with luke warm water. The cleansing ability was evaluated after what remained of the lipstick had dried out, and evaluated with the following criteria:

1: Cleansing very poor.
2: Cleansing somewhat poor.
3: Neither well, nor poor, cleansing.
4: Cleansing somewhat well.
5: Cleansing very well.

TABLE 1

| | Comparative Examples | | | | | Examples of the Invention | | | | |
|---|---|---|---|---|---|---|---|---|---|---|
| Sample No. | 1 | 2 | 3 | 4 | 5 | 6 | 7 | 8 | 9 | 10 |
| Sorbitol | 50 | 0 | 10 | 20 | 30 | 40 | 45 | 50 | 0 | 0 |
| Glycerin | 0 | 0 | 10 | 20 | 30 | 40 | 45 | 50 | 50 | 50 |
| POE (20) sorbitan monostearate | 0 | 10 | 10 | 10 | 10 | 10 | 10 | 10 | 0 | 0 |
| POE (40) hydrogenated castor oil | 0 | 0 | 0 | 0 | 0 | 0 | 0 | 0 | 10 | 0 |
| POE (20) Octyldodecanol | 0 | 0 | 0 | 0 | 0 | 0 | 0 | 0 | 0 | 10 |
| Final water content (in % by weight) | 50 | 90 | 80 | 70 | 60 | 50 | 45 | 40 | 45 | 40 |
| Evaluation of cleansing | 1 | 1 | 1 | 1 | 2 | 4 | 5 | 5 | 4 | 5 |

TABLE 2

| Sample No. | 11 | 12 | 13 | 14 | 15 | 16 | 17 | 18 | 19 |
|---|---|---|---|---|---|---|---|---|---|
| Sorbitol (70% in water) | 50 | 10 | 0 | 0 | 0 | 0 | 0 | 10 | 10 |
| Glycerin | 0 | 20 | 20 | 30 | 35 | 30 | 30 | 30 | 30 |
| Mannitol | 0 | 0 | 10 | 0 | 0 | 0 | 0 | 0 | 0 |
| 1,3-butylene glycol | 0 | 0 | 0 | 10 | 0 | 0 | 0 | 0 | 0 |
| Hexylene glycol | 0 | 0 | 0 | 0 | 5 | 0 | 0 | 0 | 0 |
| Dipropylene glycol | 0 | 0 | 0 | 0 | 0 | 10 | 10 | 0 | 0 |
| Polyethylene glycol (MW 1540) | 0 | 20 | 0 | 0 | 0 | 0 | 0 | 0 | 0 |
| POE (20) isohexadecyl ether | 0 | 0 | 15 | 5 | 5 | 5 | 5 | 0 | 0 |
| POE (60) hydrogenated castor oil | 0 | 0 | 0 | 30 | 30 | 5 | 0 | 0 | 0 |
| POE (20) sorbitan monostearate | 10 | 0 | 0 | 0 | 0 | 0 | 0 | 0 | 0 |
| POE (40) hydrogenated castor oil | 0 | 0 | 10 | 0 | 0 | 0 | 0 | 0 | 0 |
| POE (25) Octyldodecanol | 10 | 0 | 0 | 0 | 0 | 0 | 0 | 0 | 0 |
| POE (20) Sorbitan monoisostearate | 0 | 10 | 0 | 0 | 0 | 0 | 0 | 0 | 0 |
| POE (40) Sorbitan diisostearate | 0 | 0 | 0 | 0 | 0 | 0 | 30 | 0 | 0 |
| POE (75) coconut oil | 0 | 0 | 0 | 0 | 0 | 0 | 0 | 15 | 15 |
| Dimethicone copolyol (HLB 13) | 0 | 0 | 0 | 0 | 0 | 0 | 0 | 15 | 0 |
| Dimethicone copolyol (HLB 16) | 0 | 0 | 0 | 0 | 0 | 0 | 0 | 0 | 15 |
| Magnesium laureth sulfate (30% in H₂O) | 0 | 0 | 0 | 0 | 0 | 0 | 5 | 0 | 0 |
| Sodium methyl taurate (30% in water) | 0 | 0 | 0 | 0 | 0 | 0 | 0 | 5 | 0 |
| Sodium laureth (3) sulfate (50% in water) | 0 | 0 | 0 | 0 | 0 | 0 | 0 | 0 | 5 |
| Water | 30 | 40 | 45 | 25 | 25 | 50 | 20 | 25 | 25 |
| Final water content (in % by weight) | 45 | 43 | 45 | 25 | 25 | 50 | 23.5 | 31.5 | 30.5 |
| Evaluation of cleansing | 4 | 4 | 4 | 4 | 5 | 4 | 5 | 5 | 5 |

TABLE 3

| Sample No. | 20 | 21 | 22 | 23 | 24 | 25 | 26 | 27 | 28 | 29 | 30 | 31 |
|---|---|---|---|---|---|---|---|---|---|---|---|---|
| Sorbitol (70% in water) | 65 | 65 | 65 | 65 | 65 | 65 | 65 | 65 | 65 | 65 | 20 | 65 |
| Glycerin | 0 | 0 | 0 | 0 | 0 | 0 | 0 | 0 | 0 | 0 | 30 | 0 |
| Polyethylene glycol (MW 1450) | 0 | 0 | 0 | 0 | 0 | 0 | 0 | 0 | 0 | 0 | 15 | 0 |
| POE (15) Sorbitan monostearate | 0 | 0 | 0 | 0 | 0 | 0 | 10 | 0 | 0 | 0 | 0 | 0 |
| POE (20) Sorbitan monostearate | 0 | 0 | 0 | 0 | 0 | 0 | 0 | 0 | 0 | 0 | 0 | 10 |
| POE (60) Sorbitan monostearate | 0 | 0 | 0 | 0 | 0 | 0 | 0 | 10 | 0 | 0 | 0 | 0 |
| POE (80) Sorbitan monostearate | 0 | 0 | 0 | 0 | 0 | 0 | 0 | 0 | 10 | 0 | 0 | 0 |
| POE (40) Sorbitan diisostearate | 0 | 0 | 0 | 0 | 0 | 0 | 0 | 0 | 0 | 10 | 10 | 0 |
| POE (20) Sorbitan monopalmitate | 10 | 0 | 0 | 0 | 0 | 0 | 0 | 0 | 0 | 0 | 0 | 0 |
| POE (20) Sorbitan monooleate | 0 | 10 | 0 | 0 | 0 | 0 | 0 | 0 | 0 | 0 | 0 | 0 |
| POE (20) Sorbitan monolaurate | 0 | 0 | 10 | 0 | 0 | 0 | 0 | 0 | 0 | 0 | 0 | 0 |
| Dimethicone copolyol (HLB 20) | 0 | 0 | 0 | 10 | 0 | 0 | 0 | 0 | 0 | 0 | 0 | 0 |
| Dimethicone copolyol (HLB 13) | 0 | 0 | 0 | 0 | 10 | 0 | 0 | 0 | 0 | 0 | 0 | 0 |
| Dimethicone copolyol (HLB 11) | 0 | 0 | 0 | 0 | 0 | 10 | 0 | 0 | 0 | 0 | 0 | 0 |
| Water | 25 | 25 | 25 | 25 | 25 | 25 | 25 | 25 | 25 | 25 | 25 | 25 |
| Final water content (in % by weight) | 44.5 | 44.5 | 44.5 | 44.5 | 44.5 | 44.5 | 44.5 | 44.5 | 44.5 | 44.5 | 31 | 44.5 |
| Evaluation of cleansing | 5 | 5 | 4 | 5 | 5 | 5 | 5 | 5 | 4 | 5 | 5 | 5 |

TABLE 4

| Sample No. | 32 | 33 | 34 | 35 | 36 | 37 | 38 | 39 | 40 | 41 | 42 | 43 |
|---|---|---|---|---|---|---|---|---|---|---|---|---|
| Sorbitan (70% in water) | 65 | 65 | 0 | 0 | 0 | 0 | 0 | 50 | 85 | 0 | 0 | 0 |
| Glycerin | 0 | 0 | 0 | 0 | 0 | 0 | 40 | 0 | 0 | 60 | 0 | 0 |
| Polyethylene glycol (MW 1450) | 0 | 0 | 40 | 0 | 0 | 0 | 0 | 0 | 0 | 0 | 0 | 0 |
| Xylitol | 0 | 0 | 0 | 0 | 40 | 0 | 0 | 0 | 0 | 0 | 60 | 0 |
| Sucrose | 0 | 0 | 0 | 0 | 0 | 40 | 0 | 0 | 0 | 0 | 0 | 0 |
| Glucose | 0 | 0 | 0 | 0 | 0 | 0 | 0 | 0 | 0 | 0 | 0 | 35 |
| Methyl gluceth 10* | 0 | 0 | 0 | 40 | 0 | 0 | 0 | 0 | 0 | 0 | 0 | 0 |
| POE (20) stearyl alcohol | 10 | 0 | 0 | 0 | 0 | 0 | 0 | 0 | 0 | 0 | 0 | 0 |
| POE (20) Cetearyl alcohol | 0 | 10 | 0 | 0 | 0 | 0 | 0 | 0 | 0 | 0 | 0 | 0 |
| POE (20) Sorbitan monostearate | 0 | 0 | 10 | 10 | 10 | 10 | 10 | 10 | 0 | 10 | 10 | 10 |
| POE (20) Sorbitan monoisostearate | 0 | 0 | 0 | 0 | 0 | 0 | 0 | 0 | 10 | 0 | 0 | 0 |
| POE (12) Sorbitan laurate | 0 | 0 | 0 | 0 | 0 | 0 | 0 | 10 | 0 | 0 | 0 | 0 |
| Water | 25 | 25 | 50 | 50 | 50 | 50 | 50 | 30 | 5 | 30 | 30 | 55 |
| Final water content (in % by weight) | 44.5 | 44.5 | 50 | 50 | 50 | 50 | 50 | 45 | 25.5 | 30 | 30 | 55 |
| Evaluation of cleansing | 4 | 4 | 4 | 4 | 5 | 4 | 4 | 4 | 5 | 5 | 5 | 4 |

*Methyl gluceth 10 is the FDA nomenclature for POE (10) methylglucoside.

TABLE 5

| Sample No. | 44 |
|---|---|
| POE (20) Octyldodecanol | 12.5 |
| POE(20) Sorbitan monostearate | 7.5 |
| POE(20) Sorbitan monopalmitate | 7.5 |
| Sorbitol (70% in water) | 62 |
| Polyethylene glycol (MW 3350) | 0.5 |
| Mg ethyl sulfate (30% in water) | 0.1 |
| Preservative | 0.15 |
| Thickner | 0.45 |
| Water | 9.3 |
| Total water content | 27.9 |
| Evaluation on cleansing | 5 |

Rinses very easily and the skin feels very fresh and clean.

TABLE 6

| Sample No | 45 |
|---|---|
| POE (20) Octyldodecanol | 8 |
| POE(20) Sorbitan monostearate | 7.5 |
| POE(20) Sorbitan monoisostearate | 7.5 |
| Sorbitan monostearate | 0.25 |
| Sorbitan monooleate | 0.70 |
| Cocoamide MEA | 0.20 |
| POE(20) glyceryl monoisostearate | 1 |
| Thickener | 0.85 |
| Sorbitol (70% in water) | 55 |
| Na Cocoyl methyl taurate (30% in water) | 2 |
| KCl | 0.1 |
| MgSO$_4$ | 0.2 |
| preservative/antioxidant/fragrance | 0.42 |
| Water | 16.28 |
| Total water content | 32.78 |
| Evaluation on cleansing | 5 |

Rinses very easily and the skin feels veryfresh and clean after drying.

TABLE 7

| Sample No. | 46 |
|---|---|
| POE (20) Octyldodecanol | 9.7 |
| POE(20) Sorbitan monostearate | 7.5 |
| POE(20) Sorbitan monoisostearate | 7.5 |
| Sorbitan monostearate | 0.25 |
| Sorbitan monooleate | 0.7 |
| Thickener/preservative/antioxidant | 0.8 |
| Cocoamido MEA | 0.2 |
| Sorbitol (70% in water) | 65.0 |
| Mg laureth sulfate | 0.5 |
| KCl | 0.1 |

TABLE 7-continued

| | |
|---|---|
| MgSO$_4$ | 0.2 |
| Water | 7.55 |
| Total water content | 27.05 |
| Evaluation on cleansing | 5 |

Rinses very easily and the skin feels very fresh and clean after drying.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A cleansing composition, comprising:
   (a) 25–80%, by weight of at least one compound bearing at least one hydroxy moiety, selected from the group consisting of polyhydric alcohols;
   (b) at least one hydrophilic nonionic surfactant selected from the group consisting of polyethoxylated sorbitan esters;
   (c) no more than 55%, by weight, of water; and
   (d) 0.1% to 10%, by weight, of an anionic surfactant selected from the group consisting of sodium laureth sulfate, magnesium laureth sulfate, sodium methyl taurate, sodium cocoylmethyl taurate and mixtures thereof.

2. The cleansing composition of claim 1, wherein the at least one compound bearing at least one hydroxy moiety is selected from the group consisting of sorbitol, polyethylene glycol with a weight average molecular weight of at least 1000, xylitol, maltitol, mannitol, glycerine, arabitol, erythritol, diglycerine, triglycerine, hexaglycerine, decaglycerine, polyoxyethylene methylglucoside, 1,3 butylene glycol, hexylene glycol, dipropylene glycol and polyethylene methyl glucoside.

3. The cleansing composition of claim 1, wherein the at least one compound bearing at least one hydroxy moiety, is selected from the group consisting of polyethylene glycol with a weight average molecular weight of at least 1000, xylitol or glycerine.

4. The cleansing composition of claim 1, wherein the at least one hydrophilic nonionic surfactant is a polyethoxylated sorbitan fatty acid ester of a fatty acid with a branched or straight chain alkyl group of 12–18 carbon atoms, with 15–80 ethoxy moieties per molecule.

5. The cleansing composition of claim 1, wherein the at least one hydrophilic nonionic surfactant is polyethoxylated sorbitan monofatty acid ester having 15–40 ethoxy moieties per molecule.

6. The cleansing composition of claim 1, wherein the cleansing composition comprises 5–45%, by weight, of water.

7. The cleansing composition of claim 1, wherein the cleansing composition contains 35–75%, by weight, of the at least one compound bearing at least one hydroxy moiety.

8. The cleansing composition of claim 1, comprising 5–75%, by weight, of the at least one hydrophilic nonionic surfactant.

9. The cleansing composition of claim 1, comprising 5–55% by weight of the at least one hydrophilic nonionic surfactant.

10. The cleansing composition of claim 1, wherein the cleansing composition does not further comprise an oleaginous liquid.

11. The cleansing composition of claim 1, wherein the cleansing composition is a single phase liquid.

12. The cleansing composition of claim 1, wherein the cleansing composition washes off of human skin with water, without leaving a greasy or oily residue.

13. The cleansing composition of claim 1, comprising at least two compounds selected from the group consisting of polyhydric alcohols.

14. The cleansing composition of claim 1, comprising at least two hydrophilic nonionic surfactants.

15. The cleansing composition of claim 1, comprising 0.1–5% by weight, of said anionic surfactant.

16. The cleansing composition of claim 1, further comprising at least one member selected from the group consisting of UV absorbers, fragrances, pigments, dyes, opacifiers, thickening agents, antiseptics, antioxidants and insect repellents.

17. A cleansing composition, comprising:
   (a) 35–80%, by weight of at least one compound bearing at least one hydroxy moiety, selected from the group consisting of polyhydric alcohols.
   (b) at least one hydrophilic nonionic surfactant selected from the group consisting of polyethoxylated sorbitan esters;
   (c) no more than 55%, by weight, of water, and
   (d) 0.1–10%, by weight of an anionic surfactant selected from the group consisting of sodium laureth sulfate, magnesium laureth sulfate, sodium methyl taurate, sodium cocoylmethyl taurate and mixtures thereof.

18. The cleansing composition of claim 17, wherein the at least one compound bearing at least one hydroxy moiety is selected from the group consisting of sorbitol, polyethylene glycol with a weight average molecular weight of at least 1000, xylitol, maltitol, mannitol, glycerine, arabitol, erythritol, diglycerine, triglycerine, hexaglycerine, decaglycerine, polyoxyethylene methylglucoside, 1,3 butylene glycol, hexylene glycol, dipropylene glycol and polyethylene methyl glucoside.

19. The cleansing composition of claim 17, wherein the at least one hydrophilic nonionic surfactant is a polyethoxylated sorbitan fatty acid ester of a fatty acid with a branched or straight chain alkyl group of 12–18 carbon atoms, with 15–80 ethoxy moieties per molecule.

20. The cleansing composition of claim 17, wherein the cleansing composition is a single phase liquid.

21. The cleansing composition of claim 17, comprising at least two compounds selected from the group consisting of polyhydric alcohols.

22. The cleansing composition of claim 17, further comprising 0.1 . 5% by weight, of said anionic surfactant.

23. A cleansing composition, comprising:
   (a) 25–75%, by weight of at least one compound bearing at least one hydroxy moiety, selected from the group consisting of polyhydric alcohols;
   (b) 25–75%, by weight, of at least one hydrophilic nonionic surfactant selected from the group consisting of a polyethoxylated sorbitan esters;
   (c) no more than 55%, by weight, of water and,
   (d) 0.1–10%, by weight of an anionic surfactant selected from the group consisting of sodium laureth sulfate, magnesium laureth sulfate, sodium methyl taurate, sodium cocoylmethyl taurate and mixtures thereof.

24. The cleansing composition of claim 23, wherein the at least one compound bearing bearing at least one hydroxy moiety is selected from the group consisting of sorbitol, polyethylene glycol with a weight average molecular weight of at least 1000, xylitol, maltitol, mannitol, glycerine, arabitol, erythritol, diglycerine, triglycerine, hexaglycerine, decaglycerine, polyoxyethylene methylglucoside, 1,3 butylene glycol, hexylene glycol, dipropylene glycol and polyethylene methyl glucoside.

25. The cleansing composition of claim 23, wherein the at least one hydrophilic nonionic surfactant is a polyethoxylated sorbitan fatty acid ester of a fatty acid with a branched or straight chain alkyl group of 12–18 carbon atoms, with 15–80 ethoxy moieties per molecule.

26. The cleansing composition of claim 23, wherein the cleansing composition is a single phase liquid.

27. The cleansing composition of claim 23, comprising at least two compounds selected from the group consisting of polyhydric alcohols.

28. The cleansing composition of claim 23, comprising 0.1–5%, by weight, of said anionic surfactant.

29. A cleansing composition, comprising;
   (a) 25–80 %, by weight of at least one compound bearing at least one hydroxy moiety, selected from the group consisting of a polyhydric alcohol, an aldohexose, aldopentose and sucrose;
   (b) at least one hydrophilic non-ionic surfactant which is a polyethoxylated sorbitan fatty acid ester of a fatty acid with a branched or straight chain alkyl group of 12–18 carbon atoms, with 15–80 ethoxy moieties per molecule;
   (c) no more than 55%, by weight, of water; and
   (d) 0.1%–10% by weight, of an avionic surfactant selected from the group consisting of sodium laureth sulfate, magnesium laureth sulfate, sodium methyl taurate, sodium cocoylmethyl taurate and mixtures thereof.

30. The composition of claim 29, wherein said polyethoxylated sorbitan fatty acid ester is a monofatty acid ester having 15–40 ethoxy moieties per molecule.

31. The composition of claim 29, wherein said at least one compound bearing at least one hydroxy moiety is present in an amount of 35–80 %, by weight.

32. A cleansing composition, comprising:
   (a) 25–75 %, by weight of at least one compound bearing at least one hydroxy moiety, selected from the group consisting of a polyhydric alcohol, an aldohexose, an aldopentose and sucrose;
   (b) 25–75 %, by weight, of at least one hydrophilic non-ionic surfactant which is a polyethoxylated sorbitan fatty acid ester of a fatty acid with a branched or straight chain alkyl group of 12–18 carbon atoms, with 15–80 ethoxy moieties per molecule;
   (c) no more than 55%, by weight of water and;
   (d) 0.1% –10%, by weight of an anionic surfactant selected from the group consisting of sodium laureth sulfate, magnesium laureth sulfate, sodium methyl taurate, sodium cocoylmethyl taurate and mixtures thereof.

33. The cleansing composition of claim 32, wherein said cleansing composition is a single phase liquid.

34. A cleansing composition, comprising;
   (a) 25–80 %, by weight of at least one compound bearing at least one hydroxy moiety, selected from the group consisting of a polyhydric alcohol, an aldohexose, an aldopentose and sucrose;
   (b) at least one hydrophilic non-ionic surfactant selected from the group consisting of a polyethoxylated sorbitan ester, a dimethicone co-polymer, a polyethoxylated fatty alcohol and a polyethoxylated triglyceride;
   (c) No more than 55%, be weight of water; and
   (d) 0.1%–10%, by weight, of an anionic surfactant selected from the group consisting of sodium laureth sulfate, magnesium laureth sulfate, sodium methyl taurate, sodium cocoylmethyl taurate and mixtures thereof, wherein said composition is a single phase liquid.

35. A cleansing composition consisting essentially of:
   (a) 25–80 %, by weight of at least one compound bearing at least one hydroxy moiety, selected from the group consisting of a polyhydric alcohol, an aldohexose, an aldopentose and sucrose;
   (b) at least one hydrophilic non-ionic surfactant selected from the group consisting of a polyethoxylated sorbitan ester, a dimethicone co-polymer, a polyethoxylated fatty alcohol and polyethoxylated triglyceride;
   (c) no more than 55%, by weight, of water; and
   (d) 0.1–10%, by weight, of an anionic surfactant selected from the group consisting of sodium laureth sulfate, magnesium laureth sulfate, sodium methyl taurate, sodium cocoylmethyl taurate and mixtures thereof.

* * * * *